US011286321B2

(12) United States Patent
Ryu et al.

(10) Patent No.: US 11,286,321 B2
(45) Date of Patent: *Mar. 29, 2022

(54) SUPER ABSORBENT POLYMER

(71) Applicant: LG Chem, Ltd., Seoul (KR)

(72) Inventors: Chui Hee Ryu, Daejeon (KR); Hyemin Lee, Daejeon (KR)

(73) Assignee: LG Chem, Ltd.

( * ) Notice: Subject to any disclaimer, the term of this patent is extended or adjusted under 35 U.S.C. 154(b) by 0 days.

This patent is subject to a terminal disclaimer.

(21) Appl. No.: 16/282,612

(22) Filed: Feb. 22, 2019

(65) Prior Publication Data

US 2019/0183682 A1  Jun. 20, 2019

Related U.S. Application Data

(63) Continuation of application No. 14/882,619, filed on Oct. 14, 2015, now Pat. No. 10,285,866.

(30) Foreign Application Priority Data

Jan. 16, 2015  (KR) ........................ 10-2015-0007918

(51) Int. Cl.
*C08F 220/06* (2006.01)
*A61F 13/00* (2006.01)
*C08F 222/10* (2006.01)

(52) U.S. Cl.
CPC ...... *C08F 220/06* (2013.01); *A61F 13/00042* (2013.01); *C08F 222/102* (2020.02)

(58) Field of Classification Search
CPC ............ A61F 3/00042; A61F 13/00042; C08F 220/06; C08F 2222/1013; C08F 222/102
USPC .......................................... 526/307.6, 318.42
See application file for complete search history.

(56) References Cited

U.S. PATENT DOCUMENTS

| | | | |
|---|---|---|---|
| 4,446,261 A | 5/1984 | Yamasaki et al. | |
| 4,654,039 A | 3/1987 | Brandt et al. | |
| 5,760,080 A * | 6/1998 | Wada | A61F 13/15203 524/559 |
| 6,060,557 A * | 5/2000 | Dahmen | A61L 15/60 174/110 V |
| 7,173,086 B2 | 2/2007 | Smith et al. | |
| 9,114,381 B2 | 8/2015 | Lee et al. | |
| 9,433,921 B2 | 9/2016 | Ryu et al. | |
| 9,486,778 B2 | 11/2016 | Ryu et al. | |
| 2002/0120074 A1 | 8/2002 | Wada et al. | |
| 2003/0069359 A1 | 4/2003 | Torii et al. | |
| 2004/0106745 A1 | 6/2004 | Nakashima et al. | |
| 2005/0245393 A1 | 11/2005 | Herfert et al. | |
| 2006/0252913 A1 | 11/2006 | Herfert et al. | |
| 2007/0141338 A1 | 6/2007 | Ishizaki et al. | |
| 2007/0203304 A1 | 8/2007 | Mitchell | |
| 2007/0232760 A1 | 10/2007 | Fujimaru et al. | |
| 2009/0208748 A1 | 8/2009 | Torii et al. | |
| 2010/0120940 A1 | 5/2010 | Adachi et al. | |
| 2011/0290920 A1 | 12/2011 | Kim et al. | |
| 2013/0005926 A1 | 1/2013 | Kanzaki et al. | |
| 2013/0026412 A1 | 1/2013 | Machida et al. | |
| 2013/0066019 A1 | 3/2013 | Okuda et al. | |
| 2014/0031507 A1 | 1/2014 | Fukudome et al. | |
| 2014/0042364 A1 | 2/2014 | Nogi et al. | |
| 2014/0051813 A1 | 2/2014 | Won et al. | |
| 2014/0058048 A1 | 2/2014 | Won et al. | |
| 2014/0378926 A1 | 12/2014 | Ota et al. | |
| 2015/0011388 A1 | 1/2015 | Matsumoto et al. | |
| 2015/0094427 A1 | 4/2015 | Lee et al. | |
| 2015/0099624 A1 | 4/2015 | Lee et al. | |
| 2015/0259522 A1 | 9/2015 | Lee et al. | |
| 2015/0273433 A1 | 10/2015 | Nakatsuru et al. | |
| 2015/0315321 A1 | 11/2015 | Won et al. | |
| 2015/0360204 A1 | 12/2015 | Tachi et al. | |

(Continued)

FOREIGN PATENT DOCUMENTS

| | | |
|---|---|---|
| CN | 101045773 A | 10/2007 |
| EP | 1178059 A2 | 2/2002 |

(Continued)

OTHER PUBLICATIONS

Bucholtz, et al., "Modern Superabsorbent Polymer Technology," John Wiley & Sons (1998), p. 161.
Schwalm, "UV Coatings: Basics, Recent Developments and New Applications." Elsevier Science, Dec. 21, 2006, p. 115.
Odian, "Principles of Polymerization" Fourth Edition, Copyright 2004 by John Wiley & Sons, Inc.
International Search Report from PCT/KR2014/009117, dated Dec. 1, 2014.
Ryu, et al., U.S. Appl. No. 14/879,304, filed Oct. 9, 2015, entitled "Super Absorbent Polymer and Preparation Method Thereof."

(Continued)

*Primary Examiner* — Ling Siu Choi
*Assistant Examiner* — Ronald Grinsted
(74) *Attorney, Agent, or Firm* — Lerner, David, Littenberg, Krumholz & Mentlik, LLP

(57) ABSTRACT

The present invention relates to a super absorbent polymer. The super absorbent polymer according to the present invention includes surface crosslinked polymer particles prepared by surface crosslinking particles of a base resin, wherein the base resin is polymerized from water-soluble ethylene-based unsaturated monomers, and a water-soluble component, in which the water-soluble component is present in an amount of 5% by weight or less based on the total weight of the super absorbent polymer, when measured after free swelling the super absorbent polymer in a 0.9% NaCl solution for 1 hour, and the super absorbent polymer has a permeability of 50 seconds or shorter. According to the present invention, provided is a super absorbent polymer having excellent liquid permeability even when swollen without a reduction in centrifuge retention capacity or absorbency under load while having improved permeability.

8 Claims, No Drawings

(56) References Cited

U.S. PATENT DOCUMENTS

| | | |
|---|---|---|
| 2016/0053037 A1 | 2/2016 | Lee et al. |
| 2016/0175813 A1 | 6/2016 | Ryu et al. |
| 2016/0207026 A1 | 7/2016 | Lee et al. |
| 2016/0208035 A1 | 7/2016 | Ryu et al. |
| 2016/0279602 A1 | 9/2016 | Nagasawa et al. |
| 2016/0318002 A1 | 11/2016 | Lee et al. |

FOREIGN PATENT DOCUMENTS

| | | |
|---|---|---|
| EP | 2013251 B1 | 9/2011 |
| EP | 2557095 A1 | 2/2013 |
| EP | 2115016 B1 | 5/2013 |
| EP | 1837348 B1 | 9/2013 |
| EP | 2787025 A1 | 10/2014 |
| EP | 3006470 A1 | 4/2016 |
| JP | S56161408 A | 12/1981 |
| JP | S57158209 A | 9/1982 |
| JP | S57198714 A | 12/1982 |
| JP | S62054751 A | 3/1987 |
| JP | S63043912 A | 2/1988 |
| JP | H01144404 A | 6/1989 |
| JP | H03179008 A | 8/1991 |
| JP | H04120111 A | 4/1992 |
| JP | 2000026510 A | 1/2000 |
| JP | 2001089527 A | 4/2001 |
| JP | 2006055833 A | 3/2006 |
| JP | 2006522181 A | 9/2006 |
| JP | 2007-144423 A | 6/2007 |
| JP | 2007284675 A | 11/2007 |
| JP | 2007530754 A | 11/2007 |
| JP | 2007314794 A | 12/2007 |
| JP | 2008178667 A | 8/2008 |
| JP | 2009102466 A | 5/2009 |
| JP | 2009209373 A | 9/2009 |
| JP | 2009531467 A | 9/2009 |
| JP | 2011068897 A | 4/2011 |
| JP | 2013049868 A | 3/2013 |
| JP | 2013132433 A | 7/2013 |
| JP | 2013532056 A | 8/2013 |
| JP | 2016516877 A | 6/2016 |
| KR | 0183511 B1 | 4/1999 |
| KR | 2000-0063574 A | 11/2000 |
| KR | 20070004521 A | 1/2007 |
| KR | 20110049072 A | 5/2011 |
| KR | 20120054836 A | 5/2012 |
| KR | 20120059169 A | 6/2012 |
| KR | 20130093477 A | 8/2013 |
| KR | 20140024398 A | 2/2014 |
| KR | 20140126821 A | 11/2014 |
| WO | 2012102406 A1 | 8/2012 |
| WO | 2012144566 A1 | 10/2012 |
| WO | 2013122246 A1 | 8/2013 |
| WO | 2014077517 A1 | 5/2014 |
| WO | 2014112722 A1 | 7/2014 |
| WO | 2014185644 A1 | 11/2014 |

OTHER PUBLICATIONS

Third Party Observation from PCT/KR2014/009117, dated Feb. 2, 2016.

Extended Search Report from European Application 14848836.4, dated Jan. 2, 2017.

Standard Test Methods for the Nonwovens Industry, INDA and EDANA, Worldwide Strategic Partners, 2005.

* cited by examiner

SUPER ABSORBENT POLYMER

CROSS-REFERENCE TO RELATED APPLICATIONS

This application is a continuation of U.S. application Ser. No. 14/882,619 filed Oct. 14, 2015, which claims the benefit of Korean Patent Application No. 10-2015-0007918 filed on Jan. 16, 2015, the disclosures of which are herein incorporated by reference.

BACKGROUND OF THE INVENTION

(a) Field of the Invention

The present invention relates to a super absorbent polymer, and more particularly, to a super absorbent polymer having excellent liquid permeability without a reduction in other physical properties.

(b) Description of the Related Art

A super absorbent polymer (SAP) is a type of synthetic polymeric materials capable of absorbing moisture from 500 to 1000 times its own weight. Various manufacturers have denominated it as different names, such as SAM (Super Absorbency Material), AGM (Absorbent Gel Material), etc. Since such super absorbent polymers started to be practically applied in sanitary products, now they have been widely used not only for hygiene products such as disposable diapers for children, etc., but also for water retaining soil products for gardening, water stop materials for the civil engineering and construction, sheets for raising seedling, fresh-keeping agents for food distribution fields, materials for poultice or the like.

As a preparation process for such super absorbent polymers, a process by a reverse phase suspension polymerization and a process by a solution polymerization have been known. For example, Japanese Patent Laid-open Publication Nos. S56-161408, S57-158209, and S57-198714 disclose the reverse phase suspension polymerization. The process by the solution polymerization further includes a thermal polymerization method in which a polymerization gel is polymerized while being broken and cooled in a kneader equipped with a plurality of shafts, and a photo-polymerization method in which an aqueous solution with a high concentration is irradiated with UV rays onto a belt to be polymerized and dried at the same time. The hydrogel polymers thus obtained through the polymerization reaction are generally marketed in a powdery form after drying and pulverization processes.

Meanwhile, in the preparation process of the super absorbent polymer, a water-soluble component which is an uncrosslinked polymer is produced. A high content of the water-soluble component increases a liquid absorption property of the super absorbent polymer. However, when the super absorbent polymer is in contact with a liquid, it is easily eluted to make the surface sticky or to cause an unfavorable effect when being in contact with the skin. Further, if the content of the water-soluble component is high, the eluted water-soluble component generally exists on the surface of the super absorbent polymer and it makes the super absorbent polymer sticky, leading to a reduction in liquid permeability which is an ability to rapidly transfer a liquid to other super absorbent polymer.

Accordingly, there is a demand to develop a super absorbent polymer having excellent liquid permeability while maintaining high water absorption property.

SUMMARY OF THE INVENTION

In order to solve the above conventional technical problems, an aspect of the present invention is to provide a super absorbent polymer having excellent liquid permeability even when swollen without a reduction in centrifuge retention capacity or absorbency under load.

In some aspects, the present invention provides a super absorbent polymer including surface crosslinked polymer particles prepared by surface crosslinking particles of a base resin, wherein the base resin is polymerized from water-soluble ethylene-based unsaturated monomers, and a water-soluble component, wherein the water-soluble component is present in an amount of 5% by weight or less based on the total weight of the super absorbent polymer, when measured after free swelling the super absorbent polymer in a 0.9% NaCl solution for 1 hour, and wherein the super absorbent polymer has a permeability calculated by the following Equation 1 of about 50 seconds or shorter:

$$\text{Permeability (sec)} = T_S - T_0 \qquad \text{[Equation 1]}$$

wherein $T_S$ (sec) is the time required for an amount of a 0.9% saline solution to permeate a saline-absorbed super absorbent polymer under a load of 0.3 psi, wherein the saline-absorbed super absorbent polymer is prepared by swelling 0.2 g of super absorbent polymer powder with the 0.9% saline solution for 30 minutes, and $T_0$ (sec) is the time required for the amount of the 0.9% saline solution to flow under the load of 0.3 psi in the absence of the saline-absorbed super absorbent polymer.

According to the super absorbent polymer of the present invention, provided is a super absorbent polymer having excellent liquid permeability even when swollen without a reduction in centrifuge retention capacity or absorbency under load while having improved permeability.

DETAILED DESCRIPTION OF THE EMBODIMENTS

While the present invention is susceptible to various modifications and alternative forms, specific embodiments will be illustrated and described in detail as follows. It should be understood, however, that the description is not intended to limit the present invention to the particular forms disclosed, but on the contrary, the intention is to cover all modifications, equivalents, and alternatives falling within the spirit and scope of the invention.

In addition, the term 'include' or 'comprise' means that it includes a particular component (or particular element) without particular limitations unless otherwise mentioned in the present entire disclosure, and it cannot be interpreted as it excludes the addition of the other components.

As used herein, the term "particle size" refers to a sieve size used to partition the particles, unless otherwise specified.

As used herein, the terms "content distribution", "molecular weight distribution" or "ratio of dwt/d(log M)" refer to amounts of molecular weights present in a water-soluble component of super absorbent polymer, unless otherwise specified, and these terms can be used interchangeably.

Hereinafter, a super absorbent polymer according to an embodiment of the present invention will be described in detail.

The super absorbent polymer according to an embodiment of the present invention includes surface crosslinked polymer particles prepared by surface crosslinking particles of a base resin, wherein the base resin is polymerized from water-soluble ethylene-based unsaturated monomers, and a water-soluble component, wherein the water-soluble component is present in an amount of 5% by weight or less based on the total weight of the super absorbent polymer, when measured after free swelling the super absorbent polymer in a 0.9% NaCl solution for 1 hour, and wherein the super absorbent polymer has a permeability calculated by the following Equation 1 of about 50 seconds or shorter:

$$\text{Permeability (sec)} = T_S - T_0 \quad \text{[Equation 1]}$$

wherein $T_S$ (sec) is the time required for an amount of a 0.9% saline solution to permeate a saline-absorbed super absorbent polymer under a load of 0.3 psi, wherein the saline-absorbed super absorbent polymer is prepared by swelling 0.2 g of super absorbent polymer powder with the 0.9% saline solution for 30 minutes, and $T_0$ (sec) is the time required for the amount of the 0.9% saline solution to flow under the load of 0.3 psi in the absence of the saline-absorbed super absorbent polymer.

During a preparation process of the super absorbent polymer, a water-soluble component which is an uncrosslinked polymer is produced. The total content of the water-soluble component and the molecular weight of the water-soluble component greatly differ depending on the content of an initiator, polymerization temperature, content of a crosslinking agent, conditions for a surface crosslinking process, etc. during the polymerization.

A high content of the water-soluble component increases a water absorption property of the super absorbent polymer. However, when the super absorbent polymer is in contact with a liquid, the water-soluble component is easily eluted, and thus the surface of a diaper may become sticky or the skin may be damaged. Meanwhile, if the content of the water-soluble component is high, the eluted water-soluble component generally remains on the surface of the super absorbent polymer and makes the super absorbent polymer sticky, leading to a reduction in liquid permeability. Since the absorbency and the liquid permeability are conflicting properties, the super absorbent polymer may have very excellent physical properties by improving both of these properties. In particular, these properties are more important, for example, considering the current trend of slimness of the diaper thickness.

On the other hand, the water-soluble component in the super absorbent polymer may exist in an uncrosslinked form due to an incomplete crosslinking reaction during the polymerization. However, most of the water-soluble component may be generated by degradation of the crosslinking agent or breakage of a main polymer chain during a drying process. In this case, a free polymer chain of which one end is crosslinked but the other end is uncrosslinked, rather than a crosslinked chain, is generated, and the free polymer chain is eluted as the water-soluble component when the polymer chain is broken by heat. Such water-soluble component causes a problem of liquid permeability or discomfort in a swollen state by absorbing a liquid, when the super absorbent polymer is applied to a product such as diapers, etc.

The present inventors have paid attention to especially the content of the water-soluble component that is eluted after free swelling for 1 hour. Conventionally, quality of the super absorbent polymer has been determined by the content of the water-soluble component that is eluted after free swelling for 16 hours, and this content denotes the total content of the water-soluble component. However, the experimental results of the present invention are determined after free swelling for 1 hour. At least some experimental results, such as the content and molecular weight distribution of the water-soluble component after swelling for 16 hours may not be directly comparable to the content and molecular weight distribution of the water-soluble component after swelling for 1 hour. For example, a SAP of the present invention may have comparable experimental results to other SAPs when measured after swelling for 16 hours. However, a SAP of the present invention may not have comparable experimental result to other SAPs when measured after swelling for 1 hr. Further, it was found that physical properties greatly affecting the quality of the SAP are the content of the water-soluble component after free swelling for 1 hour, since most physical properties of the SAP, including liquid permeability, are measured based on 1 hr-swelling.

Accordingly, by controlling the total content and the content distribution according to the molecular weight of the water-soluble component, the super absorbent polymer of the present invention may have high centrifuge retention capacity and excellent liquid permeability, and the content of the water-soluble component that is eluted upon swelling may be minimized, thereby reducing discomfort.

While the super absorbent polymer is swollen, the water-soluble component in the polymer is eluted. At an initial stage, a water-soluble component having a low molecular weight is eluted, and a water-soluble component having a high molecular weight is eluted over time. In particular, upon swelling for 1 hour, a water-soluble component having molecular weights ranging from 100,000 to 300,000 g/mol are mostly eluted. Therefore, it was found that the amount of the water-soluble component upon 1 hr-swelling can be reduced by controlling the amount of the water-soluble component having a molecular weight of 100,000 to 300,000 g/mol which mainly influences the amount of the water-soluble component upon 1 hr-swelling, leading to the present invention.

In this regard, an amount of the water-soluble component base on the total weight of the super absorbent polymer may be measured in accordance with EDANA WSP 270.3, in particular, a measurement method after free swelling for 1 hour. That is, the water-soluble component may be included in an amount of 5% by weight or less, based on the total weight of the super absorbent polymer, when measured after free swelling the super absorbent polymer of the present invention with 0.9% NaCl solution for 1 hour. As used herein, "free swelling" means that the super absorbent polymer is allowed to swell without a restraining load upon absorbing the saline solution.

Further, the super absorbent polymer of the present invention may have a permeability of 50 seconds or shorter, for example, about 1 to about 50 seconds, preferably about 1 to about 40 seconds, or more preferably about 1 to about 35 seconds, which is calculated by the following Equation 1:

$$\text{Permeability (sec)} = T_S - T_0 \quad \text{[Equation 1]}$$

wherein $T_S$ (sec) is the time required for an amount of a 0.9% saline solution to permeate a saline-absorbed super absorbent polymer under a load of 0.3 psi, wherein the saline-absorbed super absorbent polymer is prepared by swelling 0.2 g of super absorbent polymer powder with the 0.9% saline solution for 30 minutes, and $T_0$ (sec) is the time required for the amount of the 0.9% saline solution to flow under the load of 0.3 psi in the absence of the saline-absorbed super absorbent polymer.

The permeability is an index showing how well a saline solution (0.9% NaCl aqueous solution) permeates the swollen super absorbent polymer, and evaluated by measuring the time taken for 0.9% saline solution to permeate after swelling 0.2 g of the super absorbent polymer powder for 30 minutes and then applying a pressure of 0.3 psi, as described in the literature (Buchholz, F. L. and Graham, A. T., "Modern Super absorbent Polymer Technology," John Wiley & Sons (1998), page 161). A more detailed description of the permeability measurement method will be given in the following Examples.

The super absorbent polymer of the present invention exhibits a high permeation rate for saline solution, and sufficient centrifuge retention capacity and absorbency under load, while having a very low content of the water-soluble component that is eluted upon swelling for 1 hour, thereby showing great improvements in the problem of sticky surface or skin discomfort. Therefore, the super absorbent polymer has a balance between conflicting physical properties of centrifuge retention capacity, permeation rate, and absorption rate, and thus it may be properly used as a filler for thin or ultrathin hygiene products.

According to an embodiment of the present invention, in the super absorbent polymer of the present invention, the water-soluble component has a ratio (dwt/d(log M)) of 0.9 or less over molecular weights (M) ranging from 100,000 to 300,000 g/mol when measured from an eluted solution after free swelling the super absorbent polymer with 0.9% NaCl solution for 1 hour.

More particularly, 1 g of the super absorbent polymer of the present invention is put in a 250 mL-Erlenmeyer flask, and swollen in 200 mL of 0.9% NaCl solution at 25° C. under shaking at 500 rpm for 1 hour. Then, the molecular weight distribution was measured by GPC. The water-soluble component having a ratio (dwt/d(log M)) over molecular weights (M) ranging from 100,000 to 300,000 g/mol, the ratio is about 0.9 or less, preferably about 0.86 or less, and more preferably about 0.8 or less.

When the super absorbent polymer has the content and the content distribution according to molecular weight of the water-soluble component as described above, the water-soluble component which is eluted upon swelling is minimized, thereby reducing discomfort.

The super absorbent polymer may have centrifuge retention capacity (CRC) of about 26 to about 32 g/g, and preferably about 27 to about 31 g/g, which is measured in accordance with EDANA WSP 241.2.

Further, the super absorbent polymer may have absorbency under load (0.7 psi AUL) of about 20 to about 26 g/g, and preferably about 22 to about 25 g/g, which is measured in accordance with EDANA WSP 242.2.

As described above, the present invention provides a super absorbent polymer having excellent liquid permeability even when swollen without a reduction in centrifuge retention capacity or absorbency under load.

The super absorbent polymer of the present invention having the above characteristics may be achieved by adjusting conditions related to internal crosslinking and surface crosslinking reactions. The total content of the water-soluble component and the molecular weight of the water-soluble component greatly differ depending on the content of an initiator, polymerization temperature, content of a crosslinking agent, conditions for a surface crosslinking process, etc. during the polymerization. The conventional method for controlling the water-soluble component is a method of carrying out a post-process such as neutralization after polymerization of the base resin, mixing with an additive, or increasing the content of the crosslinking agent, etc. However, these methods are disadvantageous in that the overall productivity of the super absorbent polymer is reduced, or water absorption property is reduced.

Meanwhile, according to the present invention, the content distribution of the water-soluble component is adjusted by controlling the conditions for the internal crosslinking and surface crosslinking processes without an additional process or injection of an additive, thereby optimizing water absorption property of the super absorbent polymer and physical properties of the water-soluble component, leading to preparation of a balanced polymer.

According to an embodiment of the present invention, therefore, the super absorbent polymer of the present invention may be prepared by a preparation method including the steps of performing thermal polymerization or photo-polymerization of a monomer composition containing water-soluble ethylene-based unsaturated monomers and a polymerization initiator so as to prepare a hydrogel polymer; drying the hydrogel polymer; pulverizing the dried polymer; and performing a surface crosslinking reaction by heating a mixture of the pulverized polymer with a surface crosslinking solution containing a surface crosslinking agent and water at 180 to 200° C.

In the preparation method of the super absorbent polymer of the present invention, the monomer composition which is a raw material of the super absorbent polymer includes the water-soluble ethylene-based unsaturated monomers and the polymerization initiator.

The water-soluble ethylene-based unsaturated monomer may be any monomer that is typically used in the preparation of the super absorbent polymer without limitation. Herein, one or more monomers selected from the group consisting of an anionic monomer and salts thereof, a nonionic hydrophilic monomer and an amino group-containing unsaturated monomer, and a quaternary compound thereof may be used.

Specifically, one or more selected from the group consisting of an anionic monomer such as acrylic acid, methacrylic acid, maleic anhydride, fumaric acid, crotonic acid, itaconic acid, 2-acryloylethane sulfonic acid, 2-methacryloylethane sulfonic acid, 2-acryloylpropane sulfonic acid, 2-methacryloylpropane sulfonic acid, 2-acrylamide-2-methyl propane sulfonic acid or 2-methacrylamide-2-methyl propane sulfonic acid, and salts thereof; a nonionic hydrophilic monomer such as acrylamide, methacrylamide, N-substituted acrylate, N-substituted methacrylate, 2-hydroxyethylacrylate, 2-hydroxyethylmethacrylate, 2-hydroxypropylacrylate, 2-hydroxypropylmethacrylate, methoxy polyethylene glycol acrylate, methoxy polyethylene glycol methacrylate, polyethylene glycol acrylate or polyethylene glycol methacrylate; and an amino group-containing unsaturated monomer such as (N,N)-dimethylaminoethylacrylate, (N,N)-dimethylaminoethylmethacrylate, (N,N)-dimethylaminopropylacrylamide or (N,N)-dimethylaminopropylmethacrylamide, and a quaternary compound thereof may be used.

More preferably, acrylic acid or salts thereof, for example, acrylic acid or alkali metal salts such as sodium salts thereof may be used, and it is possible to prepare a super absorbent polymer having superior physical properties by using these monomers. When the alkali metal salt of acrylic acid is used as the monomer, acrylic acid may be used after neutralized with a basic compound such as caustic soda (NaOH). The basic compound may be used in an amount of about 20 to 60 parts by weight, preferably about 30 to 50 parts by weight, based on 100 parts by weight of the acrylic acid.

The concentration of the water-soluble ethylene-based unsaturated monomer may be about 20 to about 60% by weight, preferably about 40 to about 50% by weight, based on the monomer composition. The monomer composition may include a solvent, and the concentration may be properly controlled, considering polymerization time and reaction conditions. However, if the monomer concentration is too low, the yield of the super absorbent polymer may become low and an economic problem may occur. On the contrary, if the concentration is too high, there is a process problem that a part of the monomers is precipitated, or pulverization efficiency is lowered upon pulverization of the polymerized hydrogel polymer, and the physical properties of the super absorbent polymer may be reduced.

In the preparation method of the super absorbent polymer of the present invention, the polymerization initiator used in polymerization is not particularly limited, as long as it is generally used in the preparation of the super absorbent polymer.

Specifically, the polymerization initiator may be a thermal polymerization initiator or a photo-polymerization initiator by UV irradiation, depending on a polymerization method. However, even though the photo-polymerization is performed, a certain amount of heat is generated by UV irradiation or the like and is also generated with exothermic polymerization reaction. Therefore, the thermal polymerization initiator may be further included.

As the photo-polymerization initiator, a compound capable of forming radicals by a light such as UV may be used without limitations in the constitution.

For example, one or more selected from the group consisting of benzoin ether, dialkyl acetophenone, hydroxyl alkylketone, phenyl glyoxylate, benzyl dimethyl ketal, acyl phosphine, and α-aminoketone may be used as the photo-polymerization initiator. Meanwhile, as the specific example of acyl phosphine, commercialized Lucirin TPO, namely, 2,4,6-trimethyl-benzoyl-trimethyl phosphine oxide, may be used. More various photo-polymerization initiators are well disclosed in "UV Coatings: Basics, Recent Developments and New Application (Elsevier, 2007)" written by Reinhold Schwalm, p115, however, they are not limited to the above described examples.

The concentration of the photo-polymerization initiator may be about 0.01 to about 1.0% by weight, based on the monomer composition. If the concentration of the photo-polymerization initiator is too low, a polymerization rate may become low. If the concentration of the photo-polymerization initiator is too high, the molecular weight of the super absorbent polymer may be decreased and its physical properties may be not uniform.

Further, one or more selected from the group consisting of persulfate-based initiators, azo-based initiators, hydrogen peroxide and ascorbic acid may be used as the thermal polymerization initiator. Specific examples of the persulfate-based initiators may include sodium persulfate ($Na_2S_2O_8$), potassium persulfate ($K_2S_2O_8$), ammonium persulfate (($NH_4)_2S_2O_8$) or the like. Examples of the azo-based initiators may include 2,2-azobis(2-amidinopropane)dihydrochloride, 2,2-azobis-(N,N-dimethylene)isobutyramidine dihydrochloride, 2-(carbamoylazo)isobutylonitril, 2,2-azobis(2-[2-imidazolin-2-yl]propane)dihydrochloride, 4,4-azobis-(4-cyanovaleric acid) or the like. More various thermal polymerization initiators are well-disclosed in 'Principle of Polymerization (Wiley, 1981)' written by Odian, p203, however, they are not limited to the above described examples.

The concentration of the thermal polymerization initiator may be about 0.001 to about 0.5% by weight, based on the monomer composition. If the concentration of the thermal polymerization initiator is too low, additional thermal polymerization hardly occurs, and thus the addition effect of the thermal polymerization initiator may not be sufficiently obtained. If the concentration of the thermal polymerization initiator is too high, the molecular weight of the super absorbent polymer may be decreased and its physical properties may be not uniform.

According to an embodiment of the present invention, the monomer composition may further include an internal crosslinking agent. Such internal crosslinking agent may be a crosslinking agent which has one or more of the functional group capable of reacting with a water-soluble substituent of the water-soluble ethylene-based unsaturated monomer and has one or more ethylenic unsaturated groups; or a crosslinking agent which has two or more of the functional group capable of reacting with a water-soluble substituent of the monomer and/or a water-soluble substituent formed by hydrolysis of the monomer.

Specific example of the internal crosslinking agent may include a crosslinking agent having two or more (meth)acrylate groups binding to polyol, for example, di(meth)acrylate of polyol having 2 to 20 carbon atoms, poly(meth)acrylate of polyol having 2 to 20 carbon atoms, etc. More specifically, one or more selected from the group consisting of polyethylene glycol diacrylate, hexanediol diacrylate, glycerin diacrylate, glycerin triacrylate, and trimethylol triacrylate may be used.

Such internal crosslinking agent is included at a concentration of about 0.01 to about 0.5% by weight based on the monomer composition so as to crosslink the polymerized polymer.

The super absorbent polymer of the present invention has a low content of the water-soluble component eluted upon swelling and high permeability while having proper centrifuge retention capacity and absorbency under load by controlling the kind and content of the internal crosslinking agent during polymerization of the water-soluble ethylene-based unsaturated monomers to prepare a high-strength base resin having a high crosslinking density and then by optimizing conditions for the after-mentioned surface crosslinking process of the high-strength base resin. Therefore, it may be very favorably applied to products, considering the current trend of slimness of the absorbent thickness.

In the preparation method of the present invention, the monomer composition of the super absorbent polymer may further include an additive such as a thickener, a plasticizer, a preservation stabilizer, an antioxidant, etc., if necessary.

The components of a monomer composition, such as the above described water-soluble ethylene-based unsaturated monomer, photo-polymerization initiator, thermal polymerization initiator, internal crosslinking agent and additive, can include a solvent.

In this regard, a solvent capable of dissolving the above ingredients may be used as the solvent without limitations in the constitution, and for example, one or more selected from water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethylether, toluene, xylene, butyrolactone, carbitol, methyl cellosolve acetate and N,N-dimethylacetamide may be used in combination.

The solvent may be included in any suitable amount based on the total weight of the monomer composition. In one embodiment, the solvent may be included in an amount ranging from about 20 to about 75% by weight, preferably about 40 to about 70% by weight, based on the total weight of the monomer composition.

Meanwhile, the method for forming a hydrogel polymer by thermal polymerization or photo-polymerization of the monomer composition is not particularly limited in the constitution, as long as it is a method typically used.

Specifically, the polymerization method is largely classified into the thermal polymerization and the photo-polymerization according to the polymerization energy source, and the thermal polymerization may be carried out in a reactor like a kneader equipped with agitating spindles and the photo-polymerization may be carried out in a reactor equipped with a movable conveyor belt. The above described polymerization method is an example only, and the present invention is not limited thereto.

For example, as described above, thermal polymerization is performed by providing hot air to a reactor like a kneader equipped with the agitating spindles or by heating the reactor so as to obtain the hydrogel polymer. At this time, the hydrogel polymer may have the size of centimeters or millimeters when it is discharged from the outlet of the reactor, according to the type of agitating spindles equipped in the reactor. Specifically, the hydrogel polymer may be obtained in various forms according to the concentration of the monomer composition fed thereto, the feeding speed or the like, and the hydrogel polymer having a weight average particle size of 2 to 50 mm may be generally obtained.

Further, as described above, when the photo-polymerization is carried out in a reactor equipped with a movable conveyor belt, the hydrogel polymer typically obtained may be the hydrogel polymer in a sheet-type having a width of the belt. In this regard, the thickness of the polymer sheet may vary according to the concentration of the monomer composition fed thereto and the feeding speed. Preferably, the monomer composition is fed so that the polymer sheet has a thickness of about 0.5 to about 5 cm. If the monomer composition is fed so that the thickness of the sheet-type polymer becomes too thin, the production efficiency becomes low, which is not preferred. If the thickness of the sheet-type polymer exceeds 5 cm, the polymerization reaction may not uniformly occur throughout the polymer due to the excessively high thickness.

In this regard, the hydrogel polymer thus obtained by the method may have typically a water content of about 40 to about 80% by weight. Meanwhile, the term "water content", as used herein, means a water content in the total weight of the hydrogel polymer, which is obtained by subtracting the weight of the dry polymer from the weight of the hydrogel polymer. Specifically, it is defined as a value calculated by measuring the weight loss according to evaporation of water in the polymer during the drying process of increasing the temperature of the polymer with infrared heating. In this regard, the water content is measured under the drying conditions which are determined as follows; the temperature is increased from room temperature to about 180° C. and then the temperature is maintained at 180° C., and the total drying time is determined as 20 minutes, including 5 minutes for the temperature rising step.

Next, the step of drying the hydrogel polymer thus obtained is performed.

If necessary, a coarsely pulverizing step may be performed before the drying step, in order to increase the efficiency of the drying step.

In this regard, a pulverizing device applicable may include, but the constitution is not limited, any one selected from the group consisting of a vertical pulverizer, a turbo cutter, a turbo grinder, a rotary cutter mill, a cutter mill, a disc mill, a shred crusher, a crusher, a chopper, and a disc cutter, but is not limited thereto.

In this regard, the pulverizing step may be performed so that the hydrogel polymer has a particle size of about 2 to about 10 mm.

To pulverize the polymer to have a particle size of less than 2 mm is technically not easy due to a high water content of the hydrogel polymer, and agglomeration may occur between the pulverized particles. If the polymer is pulverized to have a particle size of more than 10 mm, the effect of increasing the efficiency in the succeeding drying step may be insignificant.

The hydrogel polymer pulverized as above or immediately after polymerization without the pulverizing step is subjected to a drying process. In this regard, the drying temperature of the drying step may be about 150 to about 250° C. When the drying temperature is lower than 150° C., there is a concern that the drying time becomes excessively long or the physical properties of the super absorbent polymer finally formed may be deteriorated, and when the drying temperature is higher than 250° C., only the surface of the polymer is dried, and thus there is a concern that fine powder may be generated during the subsequent pulverization process and the physical properties of the super absorbent polymer finally formed may be deteriorated. Therefore, the drying process may be preferably performed at a temperature of about 150 to about 200° C., and more preferably about 160 to about 180° C.

Meanwhile, the drying process may be carried out for about 20 to about 90 minutes, considering the process efficiency, but is not limited thereto.

Furthermore, any known drying method may be selected and used in the drying step without limitation in the constitution if it can be generally used for drying the hydrogel polymer. Specifically, the drying step may be carried out by a method of supplying hot air, irradiating infrared rays, irradiating microwaves, irradiating ultraviolet rays or the like. When the drying step as above is finished, the water content of the polymer may be about 0.1 to about 10% by weight.

Next, the dried polymer obtained from the drying step is subjected to a pulverization step.

The polymer powder obtained from the pulverization step may have a particle size of about 150 to about 850 μm. Specific example of a milling device that can be used to achieve the above particle size may include a pin mill, a hammer mill, a screw mill, a roll mill, a disc mill, a jog mill or the like, but the present invention is not limited thereto.

The physical properties of the super absorbent polymer powder finally manufactured after the pulverization step may be properly controlled through a sorting step according to the particle size of the polymer powder obtained from the pulverization. Only a polymer having a particle size of about 150 to about 850 μm is preferably sorted and then selectively applied to the surface crosslinking reaction and finally, it is commercialized.

Next, a surface crosslinking reaction is performed by mixing the pulverized polymer with a surface crosslinking solution containing a surface crosslinking agent and water.

The surface crosslinking is a step of increasing the crosslinking density in the vicinity of the surface of the super absorbent polymer particle with regard to the internal crosslinking density of particles. In general, the surface crosslinking agent is applied to the surface of the super absorbent polymer particle. Therefore, this reaction occurs on the surface of the super absorbent polymer particle, which improves crosslinking on the surface of the particle without substantially affecting the interior of the particle. Thus, the surface-crosslinked super absorbent polymer particles have a higher level of crosslinking in the vicinity of the surface than in the interior.

In this regard, a compound capable of reacting with the functional groups of the polymer may be used as the surface crosslinking agent without limitations in the constitution.

To improve the properties of the produced super absorbent polymer, one or more selected from the group consisting of a polyhydric alcohol compound; an epoxy compound; a polyamine compound; a haloepoxy compound; a condensation product of the haloepoxy compound; an oxazoline compound; a mono-, di-, or polyoxazolidinone compound; a cyclic urea compound; a polyvalent metal salt; and an alkylene carbonate compound may be preferably used as the surface crosslinking agent.

Specific examples of the polyhydric alcohol compound may be one or more selected from the group consisting of a mono-, di-, tri-, tetra-, or polyethylene glycol, monopropylene glycol, 1,3-propanediol, dipropylene glycol, 2,3,4-trimethyl-1,3-pentanediol, polypropylene glycol, glycerol, polyglycerol, 2-butene-1,4-diol, 1,4-butanediol, 1,3-butanediol, 1,5-pentanediol, 1,6-hexanediol, and 1,2-cyclohexane dimethanol.

Further, the epoxy compound may be ethylene glycol diglycidyl ether, glycidol, etc. and the polyamine compound may be one or more selected from the group consisting of ethylene diamine, diethylene triamine, triethylene tetraamine, tetraethylene pentamine, pentaethylene hexamine, polyethylene imine, and polyamide polyamine.

Further, the haloepoxy compound may be epichlorohydrin, epibromohydrin, or α-methylephichlorohydrin. Meanwhile, the mono-, di-, or polyoxazolidinone compound may be, for example, 2-oxazolidinone.

Further, the alkylene carbonate compound may be ethylene carbonate, etc. These may be used singly or in combination. On the other hand, to increase the efficiency of the surface crosslinking process, one or more of polyhydric alcohols are preferably included in these surface crosslinking agents. More preferably, polyhydric alcohol compounds having 2 to 10 carbon atoms may be used.

The amount of the surface crosslinking agent added may be suitably controlled according to the kind of the surface crosslinking agent added or the reaction conditions, and it may be typically used in an amount of about 0.001 to about 5 parts by weight, preferably about 0.01 to about 3 parts by weight, and more preferably about 0.05 to about 2 parts by weight, based on 100 parts by weight of the polymer.

When the amount of the surface crosslinking agent used is too small, the surface crosslinking reaction hardly occurs, and when the surface cross-linking agent is used in an amount of more than 5 parts by weight based on 100 parts by weight of the polymer, the absorptivity and the physical properties may be decreased due to excessive surface crosslinking reaction.

The surface crosslinking agent may be added in the form of a surface crosslinking solution by mixing it with additional water. When water is added, there is advantageous in that the surface crosslinking agent can be evenly dispersed in the polymer. In this regard, the amount of water added thereto may be preferably about 1 to about 10 parts by weight based on 100 parts by weight of the polymer for the purpose of inducing uniform dispersion of the surface crosslinking agent, preventing agglomeration of the polymer powder, and optimizing the surface penetrating depth of the cross-linking agent at the same time.

Further, the surface crosslinking solution may further include a substance such as a metal salt, silica, etc.

With regard to the method of adding the surface crosslinking solution to the polymer, there is no limitation in the constitution. A method of adding and mixing the surface crosslinking solution and the polymer powder in a reactor, a method of spraying the surface crosslinking solution onto the polymer powder, or a method of continuously feeding the polymer and the surface crosslinking solution to a mixer which is continuously operated may be used.

As described above, the total content of the water-soluble component and the molecular weight of the water-soluble component greatly differ depending on the content of the initiator, polymerization temperature, content of the crosslinking agent, conditions for the surface crosslinking process, etc. during the polymerization. According to the present invention, a super absorbent polymer having the above described water-soluble component distribution may be prepared by controlling the temperature within a specific range during the surface crosslinking process.

According to the preparation method of the super absorbent polymer of the present invention, the surface crosslinking reaction is allowed to occur by heating the surface crosslinking solution-added polymer particles at about 180 to about 200° C., preferably at about 180 to about 190° C. When the reaction temperature is within the above range, a super absorbent polymer having the above described properties of water-soluble component may be obtained.

Further, the surface crosslinking reaction and drying may occur at the same time by heating for a crosslinking reaction time of about 15 to about 90 minutes, preferably about 20 to about 80 minutes, and more preferably about 40 to about 80 minutes. If the crosslinking reaction time is too short, sufficient crosslinking reaction may not occur, and if the crosslinking reaction time is too long, the polymer particles are damaged due to excessive surface crosslinking reaction, leading to deterioration in the physical properties.

A means for raising the temperature for surface crosslinking reaction is not particularly limited. Heating may be performed by providing a heating medium or by directly providing a heat source. In this regard, the type of the heating medium applicable may be a hot fluid such as steam, hot air, hot oil, or the like. However, the present invention is not limited thereto. The temperature of the heating medium provided may be properly controlled, considering the means of the heating medium, the heating rate, and the target temperature. Meanwhile, as the heat source provided directly, an electric heater or a gas heater may be used, but the present invention is not limited to these examples.

With regard to the super absorbent polymer of the present invention which is obtained by the above preparation method, the content of the eluted water-soluble component is 5% by weight or less based on the total weight of the super absorbent polymer, when measured after adding 1 g of the super absorbent polymer in a 250 mL-Erlenmeyer flask, and then free swelling it in 200 mL of 0.9% NaCl solution at 25° C. under shaking at 500 rpm for 1 hour.

Further, the super absorbent polymer of the present invention which is obtained by the above preparation method may have the permeability of 50 seconds or shorter, for example, about 1 to about 50 seconds, preferably about 1 to about 40 seconds, and more preferably about 1 to about 35 seconds.

Further, the water-soluble component has a ratio (dwt/d (log M)) of 0.9 or less, preferably 0.86 or less, and more preferably about 0.8 or less over molecular weights (M) ranging from 100,000 to 300,000 g/mol when measured by GPC.

Further, the super absorbent polymer of the present invention which is obtained by the above preparation method has centrifuge retention capacity of about 26 to about 32 g/g, and preferably about 27 to about 31 g/g, which is measured in accordance with EDANA WSP 241.2, and absorbency under load (0.7 psi AUL) of about 20 to about 26 g/g, and preferably about 22 to about 25 g/g, which is measured in accordance with EDANA WSP 242.2, thereby showing excellent centrifuge retention capacity and absorbency under load.

As such, the super absorbent polymer of the present invention exhibits excellent liquid permeability even when swollen without a reduction in physical properties such as centrifuge retention capacity, absorbency under load, etc.

The present invention will be described in more detail with reference to the following Examples. However, the following Examples are for illustrative purposes only, and the present invention is not intended to be limited by these Examples.

EXAMPLE

Example 1

A monomer composition in a form of aqueous solution including 100 parts by weight of acrylic acid (water-soluble ethylene-based unsaturated monomer), 30 parts by weight of NaOH, 0.03 parts by weight of potassium igacure 651 (photo-polymerization initiator), 0.5 parts by weight of polyethylene glycol diacrylate (crosslinking agent), 0.1 parts by weight of 1,6-hexanediol diacrylate (crosslinking agent), and 110 parts by weight of water as a solvent was prepared. The contents of components other than the acrylic acid were defined as parts by weight based on 100 parts by weight of the acrylic acid. The monomer composition was fed at a feed rate of 500 mL/min to 2,000 mL/min on a conveyor belt having a width of 10 cm and a length of 2 m and rotating at a speed of 50 cm/min.

While the monomer composition was fed, UV having an intensity of 10 mW/cm$^2$ was irradiated, and polymerization was allowed for 60 seconds. After polymerization, the resultant was cut with a meat chopper, and then dried using a convection oven at 160° C. for 5 hours, followed by pulverizing and sorting processes. Thus, a polymer having a particle size ranging from 150 to 850 μm was obtained.

Based on 100 parts by weight of the polymer, 0.4 parts by weight of ethylene carbonate, 5 parts by weight of methanol, and 4 parts by weight of water were mixed with each other, and then surface treatment reaction was allowed in a convection oven at 190° C. for 40 minutes so as to prepare a super absorbent polymer.

Example 2

A super absorbent polymer was prepared in the same manner as in Example 1, except that based on 100 parts by weight of the polymer of Example 1, 0.4 parts by weight of ethylene carbonate, 5 parts by weight of methanol, and 4 parts by weight of water were mixed with each other, and then surface treatment reaction was allowed in a convection oven at 200° C. for 40 minutes.

Example 3

A super absorbent polymer was prepared in the same manner as in Example 1, except that based on 100 parts by weight of the polymer of Example 1, 0.4 parts by weight of ethylene carbonate, 5 parts by weight of methanol, and 4 parts by weight of water were mixed with each other, and then surface treatment reaction was allowed in a convection oven at 180° C. for 80 minutes.

Example 4

A monomer composition in a form of aqueous solution including 100 parts by weight of acrylic acid (water-soluble ethylene-based unsaturated monomer), 30 parts by weight of NaOH, 0.03 parts by weight of potassium igacure 651 (photo-polymerization initiator), 0.5 parts by weight of polyethylene glycol diacrylate (crosslinking agent), and 110 parts by weight of water as a solvent was prepared. The contents of components other than the acrylic acid were defined as parts by weight based on 100 parts by weight of the acrylic acid. The monomer composition was fed at a feed rate of 500 mL/min to 2,000 mL/min on a conveyor belt having a width of 10 cm and a length of 2 m and rotating at a speed of 50 cm/min.

While the monomer composition was fed, UV having an intensity of 10 mW/cm$^2$ was irradiated, and polymerization was allowed for 60 seconds. After polymerization, the resultant was cut with a meat chopper, and then dried using a convection oven at 160° C. for 5 hours, followed by pulverizing and sorting processes. Thus, a polymer having a particle size ranging from 150 to 850 μm was obtained.

Based on 100 parts by weight of the polymer, 0.4 parts by weight of ethylene carbonate, 5 parts by weight of methanol, and 4 parts by weight of water were mixed with each other, and then surface treatment reaction was allowed in a convection oven at 190° C. for 40 minutes so as to prepare a super absorbent polymer.

Example 5

A super absorbent polymer was prepared in the same manner as in Example 4, except that based on 100 parts by weight of the polymer of Example 4, 0.4 parts by weight of ethylene carbonate, 5 parts by weight of methanol, and 4 parts by weight of water were mixed with each other, and then surface treatment reaction was allowed in a convection oven at 200° C. for 40 minutes.

Example 6

A super absorbent polymer was prepared in the same manner as in Example 4, except that based on 100 parts by weight of the polymer of Example 4, 0.4 parts by weight of ethylene carbonate, 5 parts by weight of methanol, and 4 parts by weight of water were mixed with each other, and then surface treatment reaction was allowed in a convection oven at 180° C. for 80 minutes.

Comparative Example 1

A monomer composition in a form of aqueous solution including 100 parts by weight of acrylic acid (water-soluble ethylene-based unsaturated monomer), 30 parts by weight of NaOH, 0.03 parts by weight of potassium igacure 651 (photo-polymerization initiator), 0.3 parts by weight of polyethylene glycol diacrylate (crosslinking agent), and 110 parts by weight of water as a solvent was prepared. The contents of components other than the acrylic acid were defined as parts by weight based on 100 parts by weight of the acrylic acid. The monomer composition was fed at a feed rate of 500 mL/min to 2,000 mL/min on a conveyor belt having a width of 10 cm and a length of 2 m and rotating at a speed of 50 cm/min.

While the monomer composition was fed, UV having an intensity of 10 mW/cm$^2$ was irradiated, and polymerization was allowed for 60 seconds. After polymerization, the resultant was cut with a meat chopper, and then dried using a convection oven at 160° C. for 5 hours, followed by pulverizing and sorting processes. Thus, a polymer having a particle size ranging from 150 to 850 μm was obtained.

Based on 100 parts by weight of the polymer, 0.4 parts by weight of ethylene carbonate, 5 parts by weight of methanol, and 4 parts by weight of water were mixed with each other, and then surface treatment reaction was allowed in a convection oven at 210° C. for 20 minutes so as to prepare a super absorbent polymer.

Comparative Example 2

A super absorbent polymer was prepared in the same manner as in Comparative Example 1, except that based on 100 parts by weight of the polymer of Comparative Example 1, 0.4 parts by weight of ethylene carbonate, 5 parts by weight of methanol, and 4 parts by weight of water were mixed with each other, and then surface treatment reaction was allowed in a convection oven at 175° C. for 90 minutes.

Comparative Example 3

A super absorbent polymer was prepared in the same manner as in Example 1, except that based on 100 parts by weight of the polymer of Example 1, 0.4 parts by weight of ethylene carbonate, 5 parts by weight of methanol, and 4 parts by weight of water were mixed with each other, and then surface treatment reaction was allowed in a convection oven at 210° C. for 20 minutes.

Comparative Example 4

A super absorbent polymer was prepared in the same manner as in Example 1, except that based on 100 parts by weight of the polymer of Example 1, 0.4 parts by weight of ethylene carbonate, 5 parts by weight of methanol, and 4 parts by weight of water were mixed with each other, and then surface treatment reaction was allowed in a convection oven at 175° C. for 90 minutes.

Comparative Example 5

A super absorbent polymer was prepared in the same manner as in Comparative Example 1, except that based on 100 parts by weight of the polymer of Comparative Example 1, 0.4 parts by weight of ethylene carbonate, 5 parts by weight of methanol, and 4 parts by weight of water were mixed with each other, and then surface treatment reaction was allowed in a convection oven at 190° C. for 40 minutes.

Comparative Example 6

A super absorbent polymer was prepared in the same manner as in Comparative Example 1, except that based on 100 parts by weight of the polymer of Comparative Example 1, 0.4 parts by weight of ethylene carbonate, 5 parts by weight of methanol, and 4 parts by weight of water were mixed with each other, and then surface treatment reaction was allowed in a convection oven at 200° C. for 40 minutes.

Comparative Example 7

A super absorbent polymer was prepared in the same manner as in Comparative Example 1, except that based on 100 parts by weight of the polymer of Comparative Example 1, 0.4 parts by weight of ethylene carbonate, 5 parts by weight of methanol, and 4 parts by weight of water were mixed with each other, and then surface treatment reaction was allowed in a convection oven at 180° C. for 80 minutes.

Experimental Example

Analysis of Water-Soluble Component

Each 1.0 g of the samples having a particle size of 150 to 850 μm was taken from the super absorbent polymers prepared in Examples and Comparative Examples and put in a 250 mL-Erlenmeyer flask, and free-swollen in 200 mL of 0.9% NaCl solution under shaking at 250 rpm for 1 hour. The aqueous solution was passed through a filter paper, and the filtrate was primarily titrated to pH 10 with 0.1 N caustic soda, and then back-titrated to pH 2.7 with 0.1 N hydrogen chloride solution. The content (% by weight) of water-soluble component in the super absorbent polymer was calculated from the obtained titration in accordance with EDANA WSP 270.3.

Further, 100 μL of the aqueous solution that was passed through a filter paper was injected into GPC instrument to measure the ratio of dwt/d(log M). GPC was performed on an instrument manufactured by Wyatt DAWN EOS, Wyatt Optilab DSP, Waters, or Wyatt, using Ultrahydrogel Linear X2 as a column, 0.1 M NaNO$_3$/0.02 M phosphate buffer as a solvent under the conditions of a flow rate of 0.8 mL/min and a temperature of 60° C., and polyacrylic acid was used as a standard.

The analysis results were obtained as dwt/d(log M) for log M (M is a molecular weight of eluted water-soluble component), and thus log M values were converted to M values, thereby obtaining dwt/d(log M) for each molecular weight of 100,000, 200,000, or 300,000.

The measurement results of the water-soluble components of Examples and Comparative Examples are shown in the following Table 1.

TABLE 1

| | Content of water-soluble component (free welling for 1 h; % by weight) | dwt/d(logM) (M: 100,000) | dwt/d(logM) (M: 200,000) | dwt/d(logM) (M: 300,000) |
| --- | --- | --- | --- | --- |
| Example 1 | 2.6 | 0.662 | 0.826 | 0.784 |
| Example 2 | 3.1 | 0.625 | 0.814 | 0.794 |
| Example 3 | 2.5 | 0.682 | 0.820 | 0.751 |
| Example 4 | 3.8 | 0.648 | 0.844 | 0.801 |
| Example 5 | 4.2 | 0.633 | 0.854 | 0.813 |
| Example 6 | 3.9 | 0.694 | 0.832 | 0.793 |
| Comparative Example 1 | 6.6 | 0.708 | 0.910 | 0.803 |
| Comparative Example 2 | 7.8 | 0.661 | 0.892 | 0.815 |
| Comparative Example 3 | 5.8 | 0.695 | 0.921 | 0.713 |

TABLE 1-continued

| | Content of water-soluble component (free welling for 1 h; % by weight) | dwt/d(logM) (M: 100,000) | dwt/d(logM) (M: 200,000) | dwt/d(logM) (M: 300,000) |
|---|---|---|---|---|
| Comparative Example 4 | 6.3 | 0.751 | 0.884 | 0.821 |
| Comparative Example 5 | 3.8 | 0.623 | 0.859 | 0.792 |
| Comparative Example 6 | 4.3 | 0.613 | 0.850 | 0.819 |
| Comparative Example 7 | 3.5 | 0.597 | 0.783 | 0.745 |

Meanwhile, for comparison with the results of the content of water-soluble component after free swelling for 1 hour, the content of water-soluble component after free swelling for 16 hours is measured for the samples of the Examples 1 to 3 and the Comparative Example 3. The content of water-soluble component after free swelling for 16 hours is measured according to the similar method to that after free swelling for 1 hour, except that Each of the samples was free-swollen in 200 mL of 0.9% NaCl solution under shaking at 250 rpm for 16 hour. The measurement results thereof are shown in the following Table 2.

TABLE 2

| | Content of water-soluble component (free welling for 16 h; % by weight) |
|---|---|
| Example 1 | 14.8 |
| Example 2 | 15.1 |
| Example 3 | 14.3 |
| Comparative Example 3 | 14.0 |

Referring to the Table 1, the Examples show the different content and molecular weight distribution of the water-soluble component after 1 hour from the Comparative Examples. However, the Examples 1 to 3 and the Comparative Example 3 do not show the substantial difference in the content of the water-soluble component after 16 hours.

Measurement of Permeability, Centrifuge Retention Capacity and Absorbency Under Load 1) Permeability Permeability was measured using a 0.9% saline solution under a load of 0.3 psi, as described in the literature (Buchholz, F. L. and Graham, A. T., "Modern Superabsorbent Polymer Technology," John Wiley & Sons (1998), page 161).

In more detail, 0.2 g of particles having a particle size of 300 to 600 μm were taken from the super absorbent polymers (hereinafter, referred to as a sample) prepared in Examples and Comparative Examples, and added to a cylinder (Φ20 mm), wherein the cylinder has a stopcock on one end, an upper limit mark and a lower limit mark thereon. The upper limit mark on the cylinder is indicated at the position of which 40 ml of (saline) solution is filled into the cylinder, and the lower limit mark on the cylinder is indicated at the position of which 20 ml of (saline) solution is filled into the cylinder.

50 g of 0.9% saline solution was added to the cylinder with the stopcock in a closed position, and left for 30 minutes. Then, if necessary, additional saline solution is added to the cylinder to bring the level of saline solution to the upper limit mark on the cylinder. Then, the cylinder including the now saline-absorbed swollen super absorbent polymers is pressurized with a load of 0.3 pounds per square inch (psi), and left for 1 minute. Thereafter, the stopcock at the bottom of the cylinder was open to measure the time taken for the 0.9% saline solution to pass from the upper limit mark to the lower limit mark on the cylinder. All measurements were carried out at a temperature of 24±1° C. and relative humidity of 50±10%.

The time taken to pass from the upper limit mark to the lower limit mark was measured for respective samples (Ts) and also measured in the absence of the super absorbent polymers ($T_0$), and permeability was calculated by the following Equation 1:

Permeability (sec)=$T_S$-$T_0$ [Equation 1]

2) Centrifuge Retention Capacity

Centrifuge retention capacity was measured in accordance with EDANA WSP 241.2. 0.2 g of the sample sorted through 30-50 mesh (particle size ranging from 300 μm to 600 μm) was put in a tea bag, and swollen in the 0.9% saline solution for 30 minutes. Then, water was removed therefrom by centrifugation at 250 G for 3 minutes, followed by weighing. Centrifuge retention capacity was determined by measuring the amount of water retained in the super absorbent polymer.

3) Absorbency Under Load (0.7 psi AUL)

Absorbency under load (0.7 psi AUL) was measured in accordance with EDANA WSP 242.2. In detail, after uniformly distributing 0.9 g of the sample of 850 to 150 μm in a cylinder regulated in the EDANA method and then pressing the sample with a pressure of 0.7 psi by using a piston and a weight, the absorbency under load was calculated as the amount of the 0.9% saline solution that was absorbed for 1 hour.

Centrifuge retention capacity, absorbency under load and permeability of Examples and Comparative Example thus measured by the above methods are shown in the following Table 2.

TABLE 2

| | Centrifuge retention capacity (g/g) | Absorbency under load (0.7 psi AUL; g/g) | Permeability (sec) |
|---|---|---|---|
| Example 1 | 28.8 | 23.9 | 21 |
| Example 2 | 27.6 | 22.8 | 14 |
| Example 3 | 28.5 | 22.9 | 33 |
| Example 4 | 30.7 | 23.5 | 41 |
| Example 5 | 30.4 | 23.8 | 41 |
| Example 6 | 31.2 | 22.9 | 48 |
| Comparative Example 1 | 34.5 | 24.9 | 363 |
| Comparative Example 2 | 38.3 | 11.2 | 948 |
| Comparative Example 3 | 27.2 | 22.5 | 71 |
| Comparative Example 4 | 31.0 | 13.4 | 851 |
| Comparative Example 5 | 34.8 | 25.5 | 153 |
| Comparative Example 6 | 33.8 | 23.2 | 123 |
| Comparative Example 7 | 34.7 | 23.8 | 161 |

Referring to Tables 1 and 2, the amount of the water-soluble component that is eluted after swelling for 1 hour is 5% by weight based on the total weight of the super absorbent polymer and permeability is 50 seconds or shorter, and therefore, the super absorbent polymer of the present invention has excellent liquid permeability even when swollen while maintaining high absorption property without a reduction in centrifuge retention capacity or absorbency under load. Accordingly, it is expected to provide the super absorbent polymer which has improvements in both conflicting properties of absorbency and liquid permeability.

What is claimed is:

1. A super absorbent polymer, comprising:
    surface crosslinked polymer particles comprising surface crosslinked particles of a base resin, wherein the base resin is polymerized from a monomer composition including water-soluble ethylene-based unsaturated monomers; and a water-soluble component,
    wherein the water-soluble component is present in an amount of 3.1% by weight or less based on the total weight of the super absorbent polymer, when measured after free swelling the super absorbent polymer in a 0.9% NaCl solution for 1 hour, and
    wherein the super absorbent polymer has a permeability calculated by the following Equation 1 of about 50 seconds or shorter:

Permeability (sec)=$TS-T0$     [Equation 1]

wherein TS (sec) is the time required for an amount of a 0.9% saline solution to permeate a saline-absorbed super absorbent polymer in a cylinder, under a load of 0.3 psi, wherein the saline-absorbed super absorbent polymer is prepared by swelling 0.2 g of super absorbent polymer powder with the 0.9% saline solution for 30 minutes, and
    T0 (sec) is the time required for the amount of the 0.9% saline solution to flow through the cylinder under the load of 0.3 psi in the absence of the saline-absorbed super absorbent polymer,
    wherein the water-soluble component has a ratio (dwt/d (log M)) of 0.9 or less over molecular weights (M) ranging from 100,000 to 300,000 g/mol, when measured from an eluted solution after free swelling 1 g of the super absorbent polymer in 200 ml of a 0.9% NaCl solution for 1 hour,
    wherein wt refers to a percent by weight of the water-soluble component in the super absorbent polymer.

2. The super absorbent polymer of claim 1, wherein a centrifuge retention capacity (CRC) ranges from about 26 to about 32 g/g.

3. The super absorbent polymer of claim 1, wherein an absorbency under load (0.7 psi AUL) ranges from about 20 to about 26 g/g.

4. The super absorbent polymer of claim 1, wherein the base resin is polymerized in the presence of an internal cross linking agent, which crosslinks polymers present in the interior of the polymer particles.

5. The super absorbent polymer of claim 4, wherein the internal cross linking agent is present in an amount ranging from 0.1 to 0.5 wt % based on the monomer composition.

6. The super absorbent polymer of claim 1, wherein surface crosslinked polymer particles are prepared by surface crosslinking particles of a base resin using a surface crosslinking solution including a surface crosslinking agent at a temperature ranging from 180 to 200° C.

7. A hygiene product including the super absorbent polymer of claim 1.

8. A disposable diaper including the super absorbent polymer of claim 1.

* * * * *